United States Patent [19]

Weber et al.

[11] Patent Number: 5,472,854
[45] Date of Patent: Dec. 5, 1995

[54] PROCESS FOR THE PRODUCTION OF 17-OXOSTEROIDS VIA THE FERMENTATIVE OXIDATION OF 17β-HYDROXYSTEROIDS BY MYCOBACTERIUM

[75] Inventors: Alfred Weber; Mario Kennekke; Uwe Klages; Klaus Nickisch; Ralph Rohde, all of Berlin, Germany

[73] Assignee: Schering Aktiengesellschaft, Berlin und Bergkamen, Germany

[21] Appl. No.: 62,034

[22] Filed: May 17, 1993

Related U.S. Application Data

[63] Continuation of Ser. No. 861,856, filed as PCT/DE91/00628 Aug. 1, 1991, abandoned.

[30] Foreign Application Priority Data

Aug. 18, 1990 [DE] Germany ............... 40 26 462.9

[51] Int. Cl.[6] ............... C12P 33/16; C12P 33/02; C12N 1/12
[52] U.S. Cl. ............... 435/55; 435/61; 435/253.1; 435/863; 435/865
[58] Field of Search ............... 435/55, 61, 253.1, 435/861, 856, 863, 865

[56] References Cited

U.S. PATENT DOCUMENTS

| 2,341,110 | 2/1994 | Mamoli | 435/61 |
| 3,395,080 | 7/1968 | Greenspan et al. | 435/55 |

FOREIGN PATENT DOCUMENTS

| 0129499 | 12/1984 | European Pat. Off. |
| 0322081 | 6/1989 | European Pat. Off. |
| 0012492 | 2/1978 | Japan | 435/55 |

OTHER PUBLICATIONS

Welsh et al. *Comput Rend. Soc. Biol.* vol. 142, 1948 p. 1074.

*Primary Examiner*—David M. Naff
*Assistant Examiner*—L. Blaine Lankford
*Attorney, Agent, or Firm*—Millen, White, Zelano & Branigan

[57] ABSTRACT

A process for the production of 17-oxosteroids by fermentative oxidation of 17β-hydroxy steroids is described, which is characterized in that for the fermentation, a bacterial culture of the species Mycobacterium spec. NRRL B-3805, Mycobacterium spec. NRRL B-3683, *Mycobacterium phlei* NRRL B-8154 or *Mycobacterium fortuitum* NRRL B-8153 is used.

15 Claims, No Drawings

PROCESS FOR THE PRODUCTION OF 17-OXOSTEROIDS VIA THE FERMENTATIVE OXIDATION OF 17β-HYDROXYSTEROIDS BY MYCOBACTERIUM

This application is a continuation of application Ser. No. 07/861,856, filed Jun. 18, 1992, which is based on international application PCT/DE91/00628 filed Aug. 1, 1991 now abandoned.

SUMMARY OF THE INVENTION

The invention relates to a process for the production of 17-oxosteroids by fermentative oxidation of 17β-hydroxy steroids.

Processes for fermentative production of 17-oxosteroids have been known for a long time. As early as 1938, A. Vercellone and L. Momoli describe a process for the production of 4-androstene-3,17-dione by fermentation of 5-androstene-3β,17β-diol (Ber. 71, 1938, 152–155). This process provides high yields of process product, when the suitable microorganisms are selected (Czech 87.068; ref. C.A. 54, 1960, 2441). There are also a great number of publications in which is described that 17-oxosteroids (such as 4-androstene-3,17-dione, 1,4-androstadiene-3,17-dione or 3-hydroxy-1,3,5(10)-estratrien-1-one) can be produced while achieving high yields by fermentative side chain catabolism of substrates, which carry a hydrocarbon chain in 17β-position.

Only very little is known about processes with whose help it is possible to oxidize 17β-hydroxy steroids microbiologically in good yield to 17-oxosteroids, without an additional conversion of the steroid taking place. M. Welsh and C. Heusghem describe a process that is to make it possible to convert estradiol with a yield of 95% to estrone, but this process cannot be done over again, since the microorganism used by these authors is not available to the public (Compt. Rend. Soc. Biol., 142, 1948, 1074).

But there is a considerable demand for making such a fermentative process available, since the chemical processes for oxidation are quite expensive. In addition, these chemical processes suffer from the shortcoming that they are performed by reagents such as pyridine and sulfur trioxide, whose environment-compatible disposal is quite problematical.

It has now been found that 17-oxosteroids surprisingly can be produced in high yields from 17β-hydroxy steroids, if bacterial cultures of the species Mycobacterium spec. NRRL B3805, Mycobacterium spec. NRRL B-3683, *Mycobacterium phlei* NRRL B-8154 or *Mycobacterium fortuitum* NRRL B-8153 are used for fermentation of the 17β-hydroxy steroids.

The process according to the invention is performed under the same fermentation conditions, which are also used with these bacterial cultures in the known microbiological conversions.

Under the culture conditions usually used for these bacterial cultures, submerged cultures are cultivated in a suitable nutrient medium with aeration. Then, the substrate (dissolved in a suitable solvent or in emulsified form) is added to the cultures and fermented, until a maximum substrate conversion is reached.

Suitable substrate solvents are, for example, methanol, ethanol, glycol monomethyl ether, dimethylformamide or dimethylsulfoxide. The emulsification of the substrate can be brought about, for example, by the latter being sprayed in micronized form or dissolved in a water-miscible solvent (such as methanol, ethanol, acetone, glycol monomethyl ether, dimethylformamide or dimethylsulfoxide) under strong turbulence in (preferably decalcified) water, which contains the usual emulsifying aids. Suitable emulsifying aids are nonionogenic emulsifiers, such as, for example, ethylenoxy adducts or fatty acid esters of polyglycols. As suitable emulsifiers, the commercially available wetting agents Tegin®, Tween® and Span® can be mentioned as examples.

The optimum substrate concentration, substrate addition time and fermentation period depend on the type of substrate and microorganism used and fermentation conditions. These values, as is generally necessary in microbiological steroid conversions, have to be determined in the individual case by preliminary tests, as they are familiar to one skilled in the art.

To perform the process according to the invention, 17β-hydroxy steroids of general formula I.

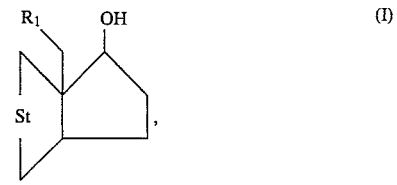

in which $R_1$ represents a hydrogen atom or a methyl group and

St symbolizes the radical of an estran-17β-ol derivative, containing up to 5 noncumulated double bonds, substituted in the 3-position by a phenolic hydroxy group, a lower alkoxy group, a lower 1-alkoxy-alkoxy group, a 2-tetrahydropyranyloxy group, or a lower alkylenedioxy group, as well as optionally in 5,10-position by an epoxy group and in 19-position optionally by a methyl group, are preferably used as substrates.

By a lower alkoxy group is preferably to be understood a group which carries up to 4 carbon atoms. Suitable alkoxy groups are, for example, the methoxy group or the tert-butyloxy group. By a lower 1-alkoxy-alkoxy group is preferably to be understood a lower alkoxy-methoxy group with an alkoxy group having up to 4 carbon atoms. For example, the 1-methoxy-methoxy group can be mentioned. By a lower alkylenedioxy group is preferably to be understood a grouping having 2 to 6 carbon atoms such as, for example, the ethylenedioxy group or the 2,2-dimethylpropylenedioxy group.

Substrates, which are suitable to perform the process according to the invention are, for example, estran-17β-ol derivatives of general formula Ia

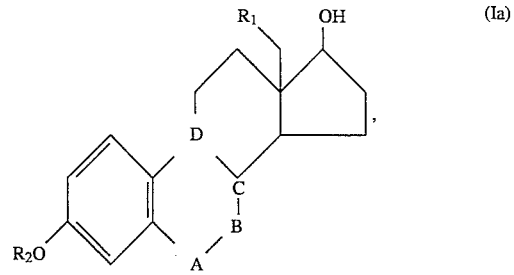

in which $R_1$ has the above-mentioned meaning, $R_2$ represents a hydrogen atom or an alkyl group containing up to 4 carbon atoms and symbolizes a grouping of partial formula

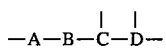

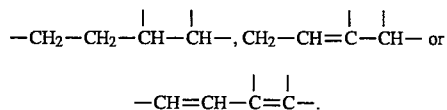

The estran-17-one derivatives formed from these substrates or the 3-hydroxy compounds obtained from this by ether cleavage are, as is known, pharmacologically effective and can, moreover, as is known, be reduced to the corresponding 17α-hydroxy compounds or be converted to the corresponding 17β-hydroxy-17α-ethinyl compounds.

Further, suitable substrates are estrane derivatives of general formula Ib

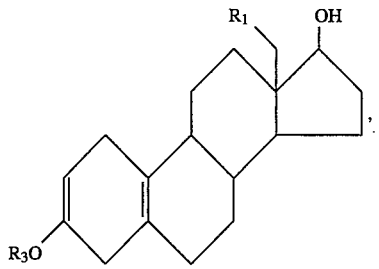

in which

.... symbolizes a single bond or a double bond, $R_1$ has the above-mentioned meaning, $R_3$ represents an alkyl group with at most 4 carbon atoms.

The 17-oxosteroids formed from these compounds can, as is known, be used, for example, to produce the pharmacologically effective 17α-ethinyl-17β-hydroxy-4-estren-3-one or its 18-methyl homologs.

Substrates worth mentioning are also those of general formula Ic

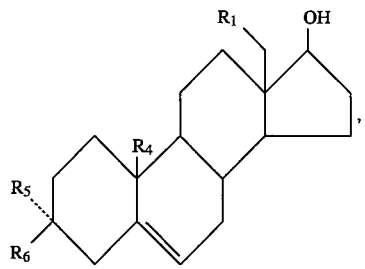

in which $R_1$ has the above-mentioned meaning, $R_4$ represents a hydrogen atom or a methyl group, $R_5$ and $R_6$ together symbolize a lower alkyldioxy group or $R_5$ means a hydrogen atom and $R_6$ represents a lower alkoxy group, a lower 1-alkoxyalkoxy group or a 2-tetrahydropyranyl group.

The 17-oxosteroids obtained from these compounds can be further processed in the same way as those of the estran-17β-ol derivatives of general formula Ic; but, on the other hand, they can also be used for the production of pregnane derivatives, as is well known to one skilled in the art.

Finally, also worth mentioning are estran-17β-ol derivatives of general formula Id

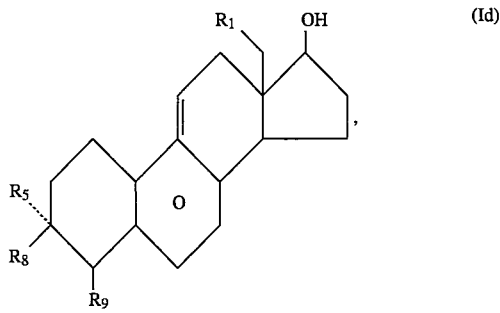

in which $R_1$ has the above-mentioned meaning, $R_9$ symbolizes a hydrogen atom and $R_7$ and $R_8$ together symbolize a lower alkylenedioxy group or $R_7$ and $R_9$ mean two hydrogen atoms or together mean a carbon-carbon bond and $R_8$ represents a lower alkoxy group, a lower 1-alkoxyalkoxy group or a 2-tetrahydropyranyloxy group.

The ketones obtained from these compounds can be converted to antigestagenically active steroids according to the process, as described in EP-A 0129499.

The following embodiments are used to explain the process according to the invention in more detail.

EXAMPLES

Example 1 a) A 500 ml Erlenmeyer with 100 ml of sterile nutrient medium containing

1% yeast extract 0.45% $Na_2HPO_4.2H_2O$ 0.34% $KH_2PO_4$ 0.2% Tween 80 with a pH of 6.7 is inoculated with a suspension of a Mycobacterium spec. NRRL B-3683 culture and shaken for 72-hours at 30° C. with 180 revolutions per minute.

b) 50 Erlenmeyers (100 ml) with 20 ml of sterile nutrient medium each containing 0.5% corn steep liquor 0.05% glucose monohydrate 0.2% yeast extract —adjusted to pH 7.0— are inoculated with 1 ml of Mycobacterium-spec.-growing culture each and incubated for 24 hours on a rotary shaker with 220 revolutions per minute at 30° C.

Then, 0.02 g of 3,3-(2,2-dimethyltrimethylenedioxy)-5,10α -epoxy-5α-estr-9(11)-en-17β-ol dissolved in 0.2 ml of dimethylformamide and sterilized by filtration is added to each culture and fermented for another 48 hours at 30° C.

c) The combined cultures are extracted with methyl isobutyl ketone and the extract is concentrated by evaporation under vacuum in a rotary evaporator at a maximum of 50° C. Then, a purification takes place by chromatography on a silica gel column.

0.85 g of 3,3-(2,2-dimethyltrimethylenedioxy)-5,10α-epoxy-5α-estr-9(11)-en-17β-one, which is identical with an authentic sample according to HPLC, is thus obtained.

Example 2 a) The production of the growing culture takes place as indicated in example 1a).

b) 50 Erlenmeyers (100 ml) with 20 ml of sterile nutrient medium each containing 2.5% corn steep liquor
0.25% soybean flour
0.3% $(NH_4)_2HPO_4$
0.25% Tween 80

—adjusted to pH 6.5— are inoculated with 1 ml of the Mycobacterium-spec.-growing culture each and incubated for 24 hours on a rotary shaker with 220 revolutions per minute at 30° C.

Then, 0.002 g of α-equilol dissolved in 0.2 ml of dimethylformamide and sterilized by filtration is added to each culture and fermented for another 72 hours at 30° C.

c) The isolation of the product takes place as described under 1c).

0.095 g of equilin, which is identical with an authentic sample according to HPLC, is thus obtained.

We claim:

1. A process for production of a 17-oxosteroid comprising subjecting a 17β-hydroxy steroid to fermentative oxidation by a bacterial culture, wherein said bacterial culture is selected from the group consisting of Mycobacterium spec. NRRL B-3805, Mycobacterium spec. NRRL B-3683, *Mycobacterium phlei* NRRL B-8154 and *Mycobacterium fortuitum* NRRL B-8153.

2. A process for the production of 17-oxosteroids according to claim 1, wherein said 17β-hydroxy steroid is of formula I

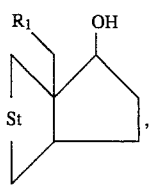
(I)

in which $R_1$ is a hydrogen atom or a methyl group; and

St is a radical of an estran-17β-ol derivative, containing up to 5 noncumulated double bonds, substituted in the 3-position by a phenolic hydroxy group, a lower alkoxy group, a lower 1-alkoxy-alkoxy group, a 2-tetrahydropyranyloxy group, or a lower alkylenedioxy group, optionally substituted in the 5,10-positions by an epoxy group, and optionally substituted in the 19-position optionally by a methyl group.

3. A process according to claim 1, wherein said bacterial culture is a culture of Mycobacterium spec. NRRL B-3805.

4. A process according to claim 1, wherein said bacterial culture is a culture of Mycobacterium spec. NRRL B-3683.

5. A process according to claim 1, wherein said bacterial culture is a culture of *Mycobacterium phlei* NRRL B-8154.

6. A process according to claim 1, wherein said bacterial culture is a culture of *Mycobacterium fortuitum* NRRL B-8153.

7. A process according to claim 2, wherein said lower alkoxy group contains up to 4 C atoms, said lower 1-alkoxy-alkoxy group is a lower alkoxy-methoxy group wherein the alkoxy group has up to 4 C atoms, and said lower alkylenedioxy group contains 2–6 C atoms.

8. A process according to claim 1, wherein said 17β-hydroxy steroid is 3,3-(2,2-dimethyltrimethylenedioxy)-5,10α-epoxy-5α-estr-9(11)-en-17β-ol.

9. A process according to claim 1, wherein said 17β-hydroxy steroid is of formula Ia

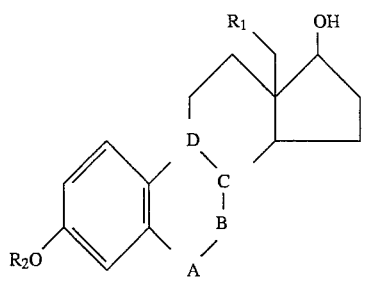

in which $R_1$ is a hydrogen atom or a methyl group;

$R_2$ is a hydrogen atom or an alkyl group containing up to 4 carbon atoms; and

symbolizes a grouping of partial formula

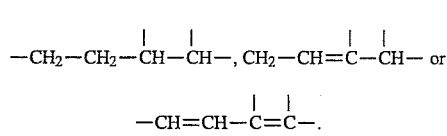

10. A process according to claim 1, wherein said 17β-hydroxy steroid is of formula Ib in which .... symbolizes a single bond or a double bond;

$R_1$ is a hydrogen atom or a methyl group; and $R_3$ is an alkyl group containing up to 4 carbon atoms.

11. A process according to claim 1, wherein said 17β-hydroxy steroid is of formula Ic

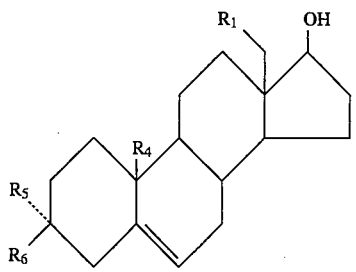

in which $R_1$ is a hydrogen atom or a methyl group;
 $R_4$ is a hydrogen atom or a methyl group;
 $R_5$ and $R_6$ together are a lower alkyldioxy group or $R_5$ is a hydrogen atom and $R_6$ is a lower alkoxy group, a lower 1-alkoxyalkoxy group or a 2-tetrahydropyranyl group.

12. A process according to claim 2, wherein said bacterial culture is a culture of Mycobacterium spec. NRRL B-3805.

13. A process according to claim 2, wherein said bacterial culture is a culture of Mycobacterium spec. NRRL B-3683.

14. A process according to claim 2, wherein said bacterial culture is a culture of *Mycobacterium phlei* NRRL B-8154.

15. A process according to claim 2, wherein said bacterial culture is a culture of *Mycobacterium fortuitum* NRRL B-8153.

* * * * *